(12) United States Patent
Austin

(10) Patent No.: US 7,918,880 B2
(45) Date of Patent: Apr. 5, 2011

(54) SELF-EXPANDING STENT AND DELIVERY SYSTEM

(75) Inventor: Michael Austin, Tuam (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 386 days.

(21) Appl. No.: 11/059,240

(22) Filed: Feb. 16, 2005

(65) Prior Publication Data

US 2006/0184226 A1 Aug. 17, 2006

(51) Int. Cl.
*A61F 2/84* (2006.01)
(52) U.S. Cl. .......................................... 623/1.11
(58) Field of Classification Search .............. 623/1.11, 623/1.12, 1.2, 1.23
See application file for complete search history.

(56) References Cited

U.S. PATENT DOCUMENTS

| | | | |
|---|---|---|---|
| 5,433,723 A * | 7/1995 | Lindenberg et al. .......... 606/198 |
| 5,749,921 A * | 5/1998 | Lenker et al. ................. 623/1.42 |
| 6,042,589 A * | 3/2000 | Marianne ...................... 606/108 |
| 6,063,112 A * | 5/2000 | Sgro ............................. 623/1.12 |
| 6,187,016 B1 * | 2/2001 | Hedges et al. ................. 606/108 |
| 6,350,278 B1 * | 2/2002 | Lenker et al. ................. 623/1.12 |
| 6,391,051 B2 | 5/2002 | Sullivan, III et al. |
| 6,514,280 B1 * | 2/2003 | Gilson .......................... 623/1.11 |
| 6,613,077 B2 | 9/2003 | Gilligan et al. |
| 6,702,843 B1 * | 3/2004 | Brown et al. ................. 623/1.11 |
| 2001/0047150 A1 | 11/2001 | Chobotov |
| 2002/0032477 A1 * | 3/2002 | Helmus et al. ................. 623/1.2 |
| 2003/0114910 A1 * | 6/2003 | Juhani Laakso et al. ..... 623/1.11 |
| 2003/0236545 A1 | 12/2003 | Gilson |
| 2003/0236565 A1 * | 12/2003 | DiMatteo et al. ............. 623/1.12 |

FOREIGN PATENT DOCUMENTS

| | | |
|---|---|---|
| DE | 10219194 | 11/2003 |
| EP | 0 943 302 A | 9/1999 |
| WO | WO 02/38084 | 5/2002 |

* cited by examiner

*Primary Examiner* — Anhtuan T Nguyen
*Assistant Examiner* — Ryan J Severson
(74) *Attorney, Agent, or Firm* — Seager, Tufte & Wickhem, LLC

(57) ABSTRACT

A medical appliance is provided that includes an outer sheath adapted to enclose a self-expanding stent in an inner space before deployment of the self-expanding stent and an inner sheath arranged between the outer sheath and the self-expanding stent before deployment of the self-expanding stent. The inner sheath includes longitudinal slits that extend from a distal end of the medical appliance to the proximal end. The longitudinal slits form a plurality of inner sleeve tails. The medical appliance also includes an actuator adapted to move the outer sheath with respect to the inner sheath during deployment of the self-expanding stent. The actuator is adapted to cause the outer sheath to move proximally. A method of deploying a self-expanding stent is provided. A method of loading a delivery mechanism is provided.

19 Claims, 8 Drawing Sheets

SELF-EXPANDING STENT AND DELIVERY SYSTEM

FIELD OF THE INVENTION

The present invention relates to medical appliances. More particularly, the present invention relates to a delivery device for a self-expanding stent, a method of using the delivery system, and a method of producing the system.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radio-opaque materials to allow for fluoroscopic visualization while placed in the body. It is also useful to coat certain devices to achieve enhanced biocompatibility and to improve surface properties such as lubriciousness.

During deployment and loading of self-expanding (SE) stents, there may be significant friction between the stent surface and the sheath. Longer stents may have higher friction forces. These shear forces may be especially damaging in relation to coated SE stents. As the application of drug eluting (DE) coatings to progressively longer stents occurs, the problems resulting from this frictional interaction may increase.

Self-expanding stents with drug-eluting coatings are being developed in increasing lengths, up to 150 mm and longer. A DE SE stent loaded in a delivery catheter may apply a compressive force against an inside surface of the delivery catheter. This compressive force may be supported directly by the coating, which may consist of a thin, relatively soft polymer carrier of the bioactive substance. During stent deployment, the compressive force combined with linear displacement may produce an abrasive, scraping action against the DE coating. This friction may also be responsible for increasing the stent deployment force, which may be increased to levels higher than are considered acceptable. These related problems may be progressively exacerbated as stent lengths increase. Additionally, a stent deployed a few minutes after being loaded may exhibit a lower stent deployment force compared with one deployed several months after being loaded.

Catheters have been reinforced with fine wire braid to increase their hoop stress, (to increase indentation resistance), and lined with thin coatings of low-friction materials such as PTFE (polytetrafluoroethylene), or alternatively, ePTFE (expanded polytetrafluoroethylene). These efforts may be problematic, particularly for the longest stents.

Deployment systems for protecting DE coatings include a rolling sheath or membrane. Although feasible, rolling sheaths or membranes may require quite difficult processes to produce and assemble the rolling membrane into the finished delivery system. At the rolling end, the membrane may turn inside out on itself and cause a load to be added to the retraction force as the outer portion of the membrane is pulled over the inner portion.

Stents with controlled expansion are apparently discussed in U.S. Pat. No. 6,613,077 to Gilligan et al., entitled "Stent with Controlled Expansion". An activation mechanism for a catheter is discussed in U.S. Pat. No. 6,391,051 to Sullivan, III et al., entitled "Pull Back Stent Delivery System with Pistol Grip Retraction Handle".

There is therefore a need for reducing deployment forces and protecting DE coatings on SE stents, in particular longer SE stents.

Each of the references cited herein is incorporated by reference herein for background information.

SUMMARY

A medical appliance is provided that includes an outer sheath adapted to enclose a self-expanding stent in an interior space before deployment of the self-expanding stent and an inner sheath enclosed within the outer sheath and adapted to be arranged about proximally adjacent to the self-expanding stent before deployment of the self-expanding stent. The medical appliance also includes a plurality of extensions coupled to a distal end of the inner sheath. The extensions are adapted to be arranged between the outer sheath and the self-expanding stent before deployment of the self-expanding stent.

In the medical appliance, the extensions may include longitudinal slits of the inner sheath forming a plurality of inner sleeve tails, the inner sleeve tails extending from a distal end of the outer sheath to a distal end of the inner sheath. The longitudinal slits of the inner sheath may be biodegradable and detachable from the medical appliance.

In the medical appliance, the extensions may include a plurality of wires, the wires extending from a distal end of the outer sheath to a distal end of the inner sheath. The medical appliance may further include a molded tip coupled to a catheter and arranged distally of the outer sheath and the self-expanding stent before deployment. The catheter may be adapted to position the medical appliance in a lumen. The molded tip may include a respective annular space for housing an end of each of the plurality of wires. The wires may include stainless steel wires. Each of the wires may be attached at a distal end to another of the wires to form a wire loop. The wires may be roll-flattened to reduce a radial displacement of the wires.

The medical appliance may further include an actuator adapted to move the outer sheath with respect to the inner sheath during deployment of the self-expanding stent. The actuator may be adapted to cause the outer sheath to move proximally.

The medical appliance may further include the self-expanding stent. A rate of expansion of the self-expanding stent may include a delay. The self-expanding stent may include a coating including a bioactive agent. The medical appliance may be deployed in a lumen of a human body and the coating of the self-expanding stent may release the bioactive agent.

During deployment, the outer sheath may be moved proximally with respect to the inner sheath and the inner sheath may allow the self-expanding stent to expand. The plurality of plurality of extensions may be retracted after the outer sheath has moved proximally and the self-expanding stent has expanded to fill a lumen.

The expandable pusher may be adapted to abut the self-expanding stent in a contracted state and oppose a proximal shear force during deployment. The expandable pusher may fit flush with an inside diameter of the inner sheath. The expandable pusher may be adapted to expand when the self-expanding stent has expanded, abut the self-expanding stent in an expanded state, and oppose a further proximal shear force during retraction of the plurality of extensions.

A method of deploying a self-expanding stent is provided that includes inserting an outer sheath into a lumen of a body. The outer sheath is coupled to a catheter and encloses an inner sheath and a plurality of extensions. The plurality of extensions is coupled to a distal end of the inner sheath and encloses the self-expanding stent. The method also includes activating an activator to move the outer sheath relative to the inner sheath and the plurality of extensions. The outer sheath moves proximally and the plurality of extensions allows the self-expanding stent to expand to an edge of the lumen.

The method may include activating the activator to move the inner sheath relative to a pusher abutting the self-expanding stent. The inner sheath and the plurality of extensions may move proximally with respect to the self-expanding stent.

The method may include retracting the catheter.

A method of loading a delivery mechanism is provided that includes inserting an inner sheath into an outer sheath. The inner sheath includes a tube having a plurality of longitudinal slits bounded at least distally by a circumferential ring. The outer sheath is coupled to a catheter. The catheter includes an activation mechanism adapted to move the outer sheath proximally with respect to an expandable pusher. The method also includes detaching each of the longitudinal slits from each other of the longitudinal slits at a distal end of the inner sheath.

The detaching operation may include severing the circumferential ring at each of the longitudinal slits to extend each longitudinal slit to a distal edge of the inner sheath.

The detaching operation may include severing a cylindrical end portion of at least the inner sleeve so that each longitudinal slit extends to a distal edge of the inner sheath.

The expandable pusher may be adapted to abut the inner sheath when the outer sheath moves proximally with respect to the expandable pusher.

The activation mechanism may include a dual action activator, a first activation adapted to move the outer sheath proximally with respect to the expandable pusher, a second activation adapted to move the inner sheath proximally with respect to the expandable pusher.

The method may include contracting a self-expanding stent and inserting the self-expanding stent into the inner sheath.

The contracting of the self-expanding stent and the inserting of the self-expanding stent into the inner sheath may be performed before the inserting of the inner sheath in the outer sheath and the detaching of each of the longitudinal slits. The inserting of the inner sheath into the outer sheath further may include inserting the self-expanding stent and the inner sheath into the outer sheath.

The contracting of the self-expanding stent and the inserting of the self-expanding stent into the inner sheath may be performed after the inserting of the inner sheath in the outer sheath and the detaching of each of the longitudinal slits.

DETAILED DESCRIPTION

Figure 1:
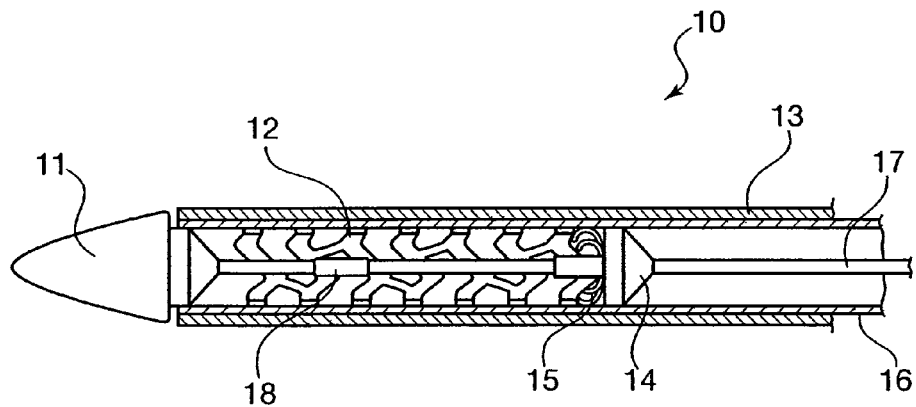
FIG. 1 is a schematic cross-sectional representation of an exemplary embodiment of the present invention showing a self-expanding stent loaded in a delivery system that includes a two-piece sheath.

The drive to exploit the application of drug-eluting coatings to self-expanding stents, and particularly to very long stents (up to 150 mm), has brought a number of challenges. Regarding stent deployment, these problems may be related to the compressive stress reaction exerted by an inside surface of the delivery catheter on the coating by the residual spring energy in the compressed, loaded stent.

The polymer base of the DE coating may thus be subjected to a continuous compressive force, which during deployment may cause a scuffing and/or abrasive action at the interface of the coating and the catheter. There may also be an increase in the stent deployment force.

In an exemplary embodiment of the present invention, an inner sheath (also referred to herein as an inner sleeve) is provided that has a plurality of longitudinal slits. Therefore, the inner sheath may open freely into the body lumen. During deployment, the inner sleeve may then be retracted, followed by the normal withdrawal from the vessel of the delivery system.

An exemplary embodiment of the present invention may utilize an inner protective sleeve with longitudinal slits. The exemplary embodiment of the present invention may utilize this non-rolling protective sleeve, which may be retracted linearly within the outer sheath and after the retraction of the outer sheath.

The inner coating protection sleeve may be made from a low friction material and may be cut longitudinally, possibly with between 2 and 6 slits. A retraction mechanism may connect the sheath and sleeve and may pull back the outer sheath fully before retracting the inner sleeve.

The inner sleeve may then be retracted past the deployed, expanded stent, in which position the coating abrasion forces may be reduced. For example, an inner sleeve of external diameter 2 mm may be cut longitudinally into 4 equally spaced, 90 degree arcs. After the outer sheath has been retracted and the stent has self-expanded to 10 mm diameter, each of the 4 inner sleeve tails may now cover an arc of approximately 18 degrees, and an arc length of 1.6 mm. Some flattening of the inner sleeve tails may occur, thereby opening the small diameter curvature of the thin-walled tails to conform to the larger diameter of curvature of the expanded stent. For an exemplary wall thickness of the inner sheath (for example, 0.001 inch to 0.0015 inch), the inner sleeve tails may reasonably conform to the curvature. For example, before any retraction of the inner sleeve, approximately 80% of the radial spring force of the stent may be carried by the artery wall, while only approximately 20% of the stent would retain the covering of the inner sleeve tails. Combined with a low friction interface between the inner sleeve tails and the stent, the retraction of the inner sleeve tails may be facilitated by this distribution of force.

An expandable stent pusher may be included in the system to ensure that the stent is deployed with a sufficient degree of linear positional precision. The design of a sequential, double sheath (also referred to herein as a sheath/sleeve combination) deployment mechanism may reduce and/or eliminate sheath retraction over a fully loaded, contracted stent.

At least three features may distinguish an exemplary embodiment of the drug-eluting, self-expanding stent delivery system provided from conventional SE stent delivery systems: first, the additional, inner expandable DE coating protection sheath; second, an expandable stent pusher; and third, a two-stage sheath retraction mechanism. An exemplary embodiment of the present invention may include some or all of these features. In a situation with a single stage retraction mechanism (in which the third feature may be absent), the inner sheath may be retracted as a result of retracting the entire catheter and deployment mechanism. However, this may result in reduced positional control for the deployed stent.

The inner DE coating protection sleeve may be a thin-walled (possibly 0.001 inch to 0.0015 inch) cylindrical tube with a diameter provided to give a close sliding fit inside the main catheter delivery sheath. This sleeve may provide a protection wall or barrier for the DE coating. When the main outer sheath is retracted, instead of sliding over the exterior of the coating with the risk of causing frictional scraping damage to the coating, the outer sheath may now freely slide off this new inner sleeve. Because the material of the inner sleeve may be selected for low sliding friction properties (for instance, PTFE), the stent deployment force may now be significantly lower than if the outer sheath were retracted over the polymer based DE coating.

Extruded tubing, as in some catheter delivery tubes, may have a dense, homogenous structure with a highly polished surface. The spray-deposited polymer coating may have a relatively soft and textured surface, which renders it more liable to scuffing and tearing damage.

The inner sleeve may function more effectively if it is able to separate and allow the stent to expand freely into the body lumen as the outer sheath is retracted.

An exemplary embodiment of the inner sleeve enabling radial opening includes multiple (for instance, between two and six) equally spaced slits, disposed in a longitudinal direction over a distance slightly longer than the stent. Due to a potentially large difference in diameter of the stent between its loaded (contracted) and deployed (expanded) conditions, the individual segments of the fully opened, slit portion of the inner sleeve may occupy a relatively small arc of the total expanded stent circumference. Thus, immediately after the retraction of the outer sheath, these inner sleeve tails may offer little resistance to their own, secondary retraction since most of the radial spring force of the deployed stent may now be supported directly by the vessel wall. This is in contrast to the initial condition of the loaded stent in which all of the radial spring force is carried directly by the inner sleeve. During the retraction of the inner sleeve, the amount of stent radial expansion force supported directly by the artery wall may progressively increase until the inner sleeve is completely retracted.

An exemplary embodiment of the present invention may include an expandable stent pusher. The operation of the inner expandable sleeve may require a compatible expandable stent pusher. In a conventional self-expanding stent delivery system, a pusher provides a buttress and shoulder against which the proximal end of the stent is held during the retraction of the outer sheath. A significant portion of the sheath retraction force may be generated from the friction force present between the compressed stent and the retracting outer sheath. In order to effect deployment and create relative linear displacement between the stent and the sheath, it may be necessary to prevent the stent from moving with the retracting outer sheath. The purpose of the stent pusher is therefore to supply this reaction force against the stent. Also, as the stent is being deployed, for instance by a physician at a particular vessel lesion site, the stent must be held without further movement relative to the vessel wall while the outer sheath is retracted relative to the stent and vessel wall.

When the operation of the inner expandable sleeve is considered in the context of an exemplary embodiment of the present invention, there may be an additional requirement for the stent pusher to be expandable. The expansion function may ensure that the retraction of the inner sleeve does not permit any migration of the stent in the body lumen. As noted above, after the initial outer sheath retraction, there may be a reduced retraction force due to the relative ease with which the several inner sleeve tails may be retracted through the stent-vessel interface. After retraction of the inner sleeve tails, the stent may bed down into the lining of the vessel wall. To avoid the risk of stent displacement, an expandable pusher may be provided. The pusher, when self-expanded to approximately the same size as the deployed stent, may supply the reaction force between the proximal end of the stent and the inner sleeve during the retraction of the inner sleeve.

In one embodiment of an expandable pusher, a plurality of fine, superelastic Nitinol wire springs (possibly between 6 and 8) may be securely mounted on the catheter inner shaft. When the stent is loaded, these springs may be contracted and loaded to occupy a space inside the inner expandable sheath. A rigid molded buttress (also referred to herein as a pusher) may be secured immediately behind the springs to support the fully opened springs and carry some of the reaction force. During stent deployment, as the outer sheath uncovers the stent and self-expanding pusher, each of the wire springs may expand so that, as the inner sleeve begins to be retracted, the enlarged pusher may supply the reaction force between the stent and the inner sheath.

An activation mechanism useful in combination with an exemplary embodiment of the present invention may provide a two-stage sheath retraction mechanism. The exemplary mechanism may provide a delayed, double linear displacement.

These three features (an inner expandable DE coating protection sheath, an expandable stent pusher, and a two-stage sheath retraction mechanism) may provide an improved stent delivery system providing a protective barrier for the drug-eluting stent coating during delivery into a body lumen.

Alternative exemplary embodiments of the present invention may include some or all of the following designs, features, or functions. A biodegradable inner protective sleeve may be provided, which may be detachable from the catheter delivery mechanism. An exemplary embodiment of the present invention may be used in combination with a short delayed self-expansion of the stent, or a stent with a reduced rate of self-expansion during deployment. A delayed expansion SE stent may further increase the ease with which the inner sleeve tails may be retracted past the stent, since the inner sleeve tails may be freely retracted past the delayed expansion or partly expanded stent.

Under certain circumstances the self-expanding pusher may also function as an embolic particle protection filter. An embolic particle protection filter may be of use in stenting procedures that may give rise to the production of loose particles of plaque from the artery lesion site. An exemplary embodiment of an embolic filter may trap particles and be effective when blood flow is towards the proximal end of the catheter. The filter may also remove trapped emboli with the withdrawal of the catheter from the artery during or after the procedure.

During product assembly, a short portion of the distal end of inner sleeve may be continuous, i.e., not slit, in order to facilitate stent loading. After the stent and inner sleeve combination has been loaded into a delivery sheath, the distal ends of the slits may be completed, forming the inner sleeve tails. This final cut may allow the inner sleeve tails to open and pass over the deployed stent.

Roll-flattening of each inner sheath tail before assembly may assist in promoting the conforming shape change. Additionally, shape-memory components may be utilized to facilitate the adaptation of the inner sleeve tails from covering the contracted SE stent to covering the expanded SE stent.

FIG. 1 is a schematic cross-sectional representation of an exemplary embodiment of the present invention showing SE stent 12 loaded in delivery system 10. Delivery system 10 includes tip 11, outer protective sheath 13, inner protective sheath 16, pusher 14, and pusher springs 15. Pusher 14 and pusher springs 15 may collectively be referred to herein as an expandable pusher. Delivery system 10 also includes activator shaft 17 and central shaft 18 positioned on a central axis of delivery system 10. Delivery system 10 is shown with SE stent 12 in a contracted (i.e., loaded) state ready to be inserted into a lumen of a body.

Figure 2:
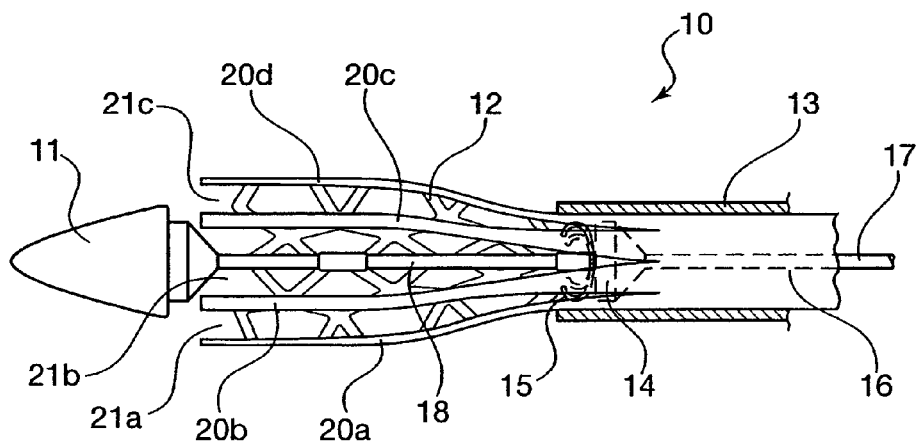
FIG. 2 shows the schematic cross-sectional representation of the exemplary embodiment of the present invention of FIG. 1 after a partial retraction of the outer sheath showing the SE stent partially expanded and the inner sheath partially expanded.

FIG. 2 shows the schematic cross-sectional representation of the exemplary embodiment of the present invention of FIG. 1 after a partial retraction of outer protective sheath 13 showing SE stent 12 partially expanded and inner protective sheath 16 partially expanded. Activation of delivery system 10 is accomplished by moving outer protective sheath 13 in a proximal direction relative to a distal motion of activator shaft 17 connected to pusher 14. As outer protective sheath 13 is retracted and exposes inner protective sheath 16, SE stent 12 is able to expand, since tails 20a, 20b, 20c, 20d (also referred to herein as inner protective sheath tails) are separated by slits 21a, 21b, 21c, 21d. Slits 21a, 21b, 21c, 21d expand as SE stent 12 expands. Since outer protective sheath 13 is withdrawn across the surface of tails 20a, 20b, 20c, 20d, which are coated with a lubricious coating (for instance, PTFE), damage to the coating on SE stent 12 is reduced and/or eliminated.

Figure 3:
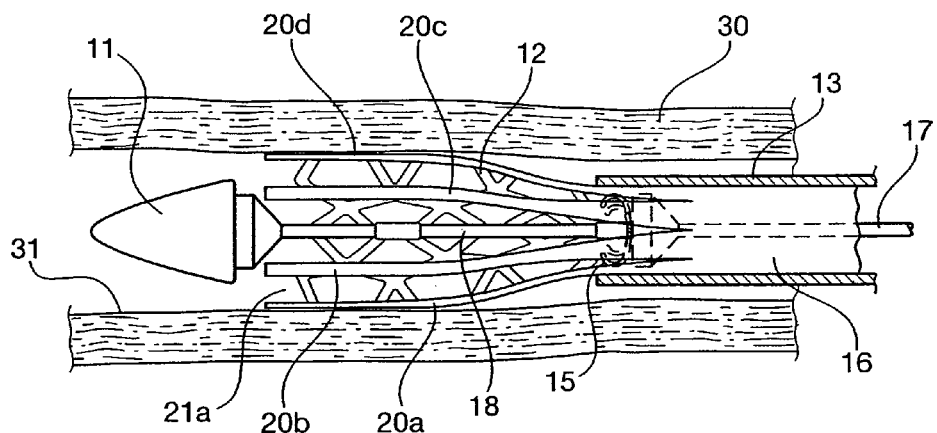
FIG. 3 shows the schematic cross-sectional representation of the exemplary embodiment of the present invention of FIG. 2 in a lumen.

FIG. 3 shows the schematic cross-sectional representation of the exemplary embodiment of the present invention of FIG. 2 in a lumen bounded by lumen wall 30. FIG. 3 shows SE stent 12 partially expanded and inner protective sheath 16 partially expanded after a partial retraction of outer protective sheath 13. SE stent 12 is adapted to expand to press against lumen wall surface 31. In FIG. 3, SE stent 12 is partially expanded causing tails 20a, 20b, 20c, 20d of inner protective sheath 16 to press against lumen wall surface 31.

Figure 4:
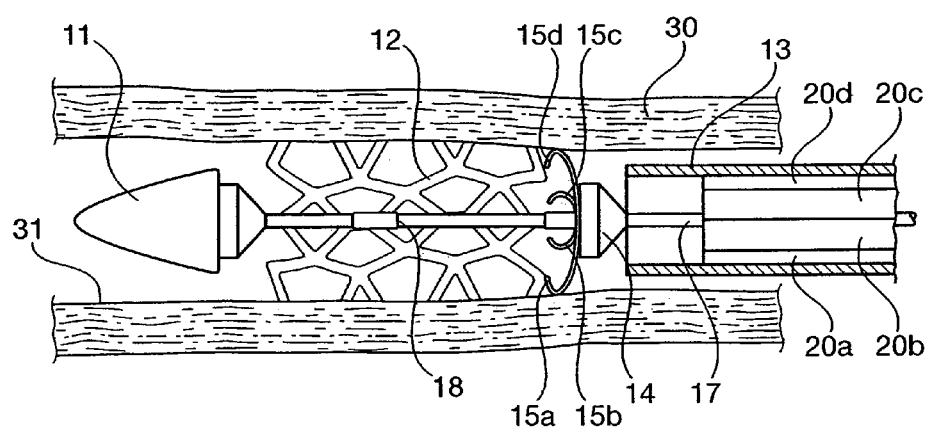
FIG. 4 shows the schematic cross-sectional representation of the exemplary embodiment of the present invention of FIG. 3 in the lumen in a fully expanded state after the retraction of the inner sheath.

FIG. 4 shows the schematic cross-sectional representation of the exemplary embodiment of the present invention of FIG. 3 in the lumen bounded by lumen wall 30 in a fully expanded state after the complete retraction of outer protective sheath 13 and after the retraction of inner protective sheath 16. SE stent 12 is fully expanded and inner protective sheath 16 is fully retracted. SE stent 12 presses against lumen wall surface 31. Pusher spring arms 15a, 15b, 15c, 15d, pressed against the edge of SE stent 12 during the retraction of tails 20a, 20b, 20c, 20d to maintain SE stent 12 in position against lumen wall surface 31.

Figure 5:
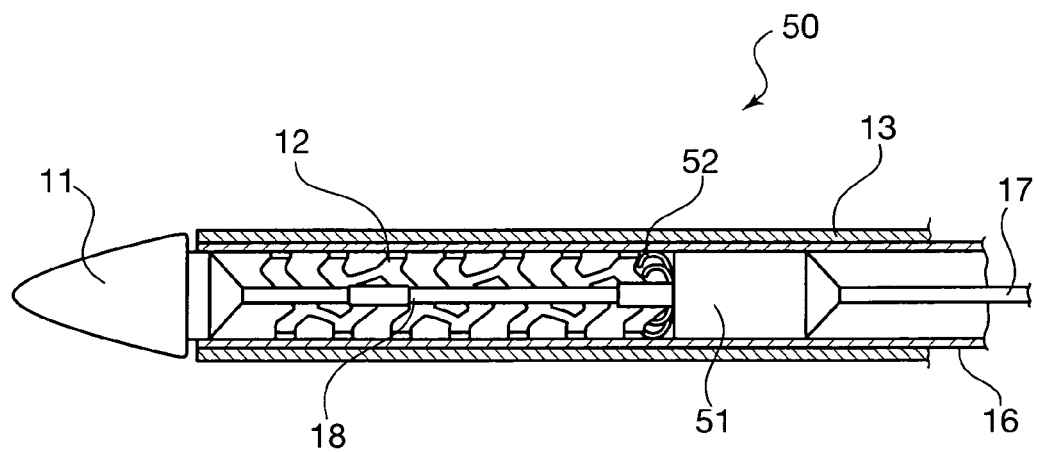
FIG. 5 is a schematic cross-sectional representation of an alternative exemplary embodiment of the present invention showing a self-expanding stent loaded in a delivery system that includes a two-piece sheath and an alternative pusher design.

FIG. 5 is a schematic cross-sectional representation of an alternative exemplary embodiment of the present invention showing SE stent 12 loaded in robust delivery system 50. Robust delivery system 50 includes tip 11, outer protective sheath 13, inner protective sheath 16, robust pusher 51, and robust pusher springs 52. Robust pusher 51 and robust pusher springs 52 may collectively be referred to herein as a robust expandable pusher. Robust delivery system 50 also includes activator shaft 17 and central shaft 18 positioned on a central axis of expanded pusher delivery system 50. Robust delivery system 50 is shown with SE stent 12 in a contracted (i.e., loaded) state ready to be inserted into a lumen of a body. Robust pusher 51 may be a longer, cylindrical pusher buttress, and may provide a stable support for robust pusher springs 52. The longer design of robust pusher 51 may assist in preventing the collapse and buckling of the ends of pusher springs 52 (distal of robust pusher 51) during retraction of outer sheath 13. Robust pusher springs 52 may be more robust than pusher springs 15, or, alternatively, may be similar to pusher springs 15.

Figure 6:
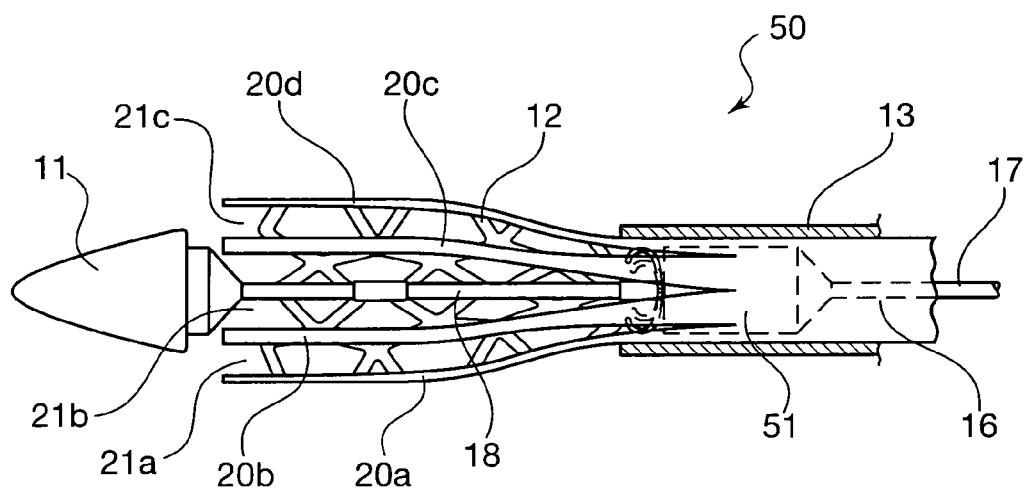
FIG. 6 shows the schematic cross-sectional representation of an exemplary embodiment of the present invention of FIG. 5 after a partial retraction of the outer sheath and showing the SE stent partially expanded and the inner sheath partially expanded.

FIG. 6 shows the schematic cross-sectional representation of an exemplary embodiment of the present invention of FIG. 5 after a partial retraction of outer protective sheath 13 and showing SE stent 12 partially expanded and inner protective sheath 16 partially expanded. Activation of expanded pusher delivery system 50 is accomplished by moving outer protective sheath 13 in a proximal direction relative to a distal motion of activator shaft 17 connected to robust pusher 51. As outer protective sheath 13 is retracted and exposes inner protective sheath 16, SE stent 12 is able to expand, since tails 20a, 20b, 20c, 20d are separated by slits 21a, 21b, 21c, 21d. Slits 21a, 21b, 21c, 21d expand as SE stent 12 expands. Since outer protective sheath 13 is withdrawn across the surface of tails 20a, 20b, 20c, 20d, which are coated with a lubricious coating, damage to the coating on SE stent 12 is reduced and/or eliminated. Robust pusher springs 52 may provide greater stability to SE stent 12 in maintaining position during the retraction of inner protective sheath 16. The function of a longer, close-fitting pusher buttress may prevent the collapse of the tails at the start of the outer sheath retraction. In the fully assembled system, the inner slits should not extend beyond the proximal end face of the pusher buttress. This may ensure that the light compressive/shear forces transmitted to the sleeve tails do not cause the tails to buckle.

Figure 7:
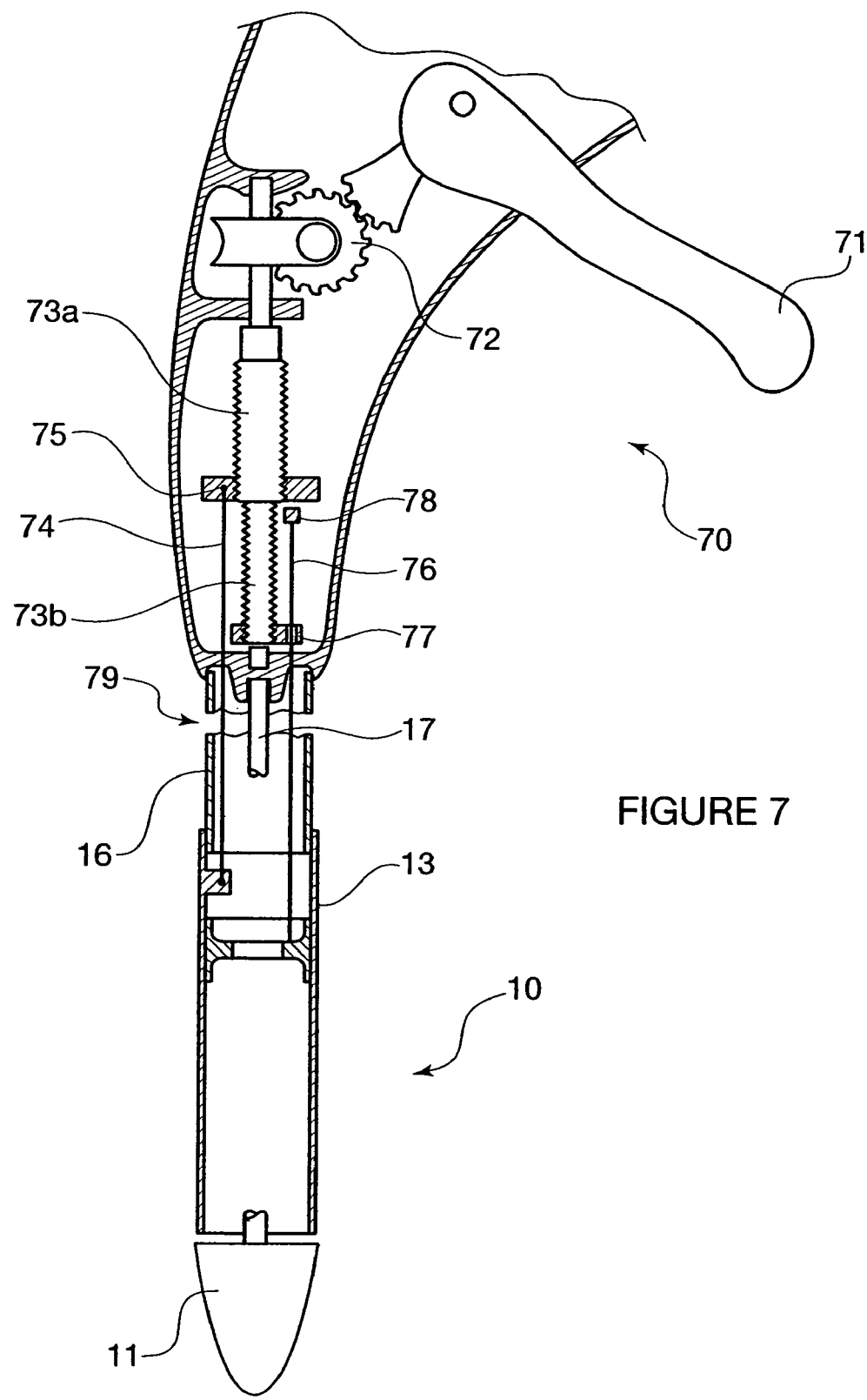
FIG. 7 is a schematic cross-sectional representation of an exemplary embodiment showing a catheter delivery mechanism in a loaded state and an activation mechanism with a portion of the catheter cut away.

FIG. 7 is a schematic cross-sectional representation of an exemplary embodiment showing delivery system 10 in a loaded state and activation mechanism 70 with a portion of the catheter cut away by break 79. Delivery system 10 includes tip 11, outer protective sheath 13, inner protective sheath 16, and activator shaft 17. Activation mechanism 70 includes lever 71 that activates gear 72 to rotate screw 73a. Gear 72 may incorporate a rotary ratchet that allows the screw drive mechanism to advance without a corresponding reverse rotation produced by the return stroke of lever 71. Screw 73a is continuous with screw 73b. Anchor 75 on screw 73a anchors wire 74 which attaches to outer protective sheath 13. Anchor 77 on screw 73b provides a delayed stop for wire 76 by stopping stop 78. Wire 76 attaches to inner protective sheath 16.

Figure 8:
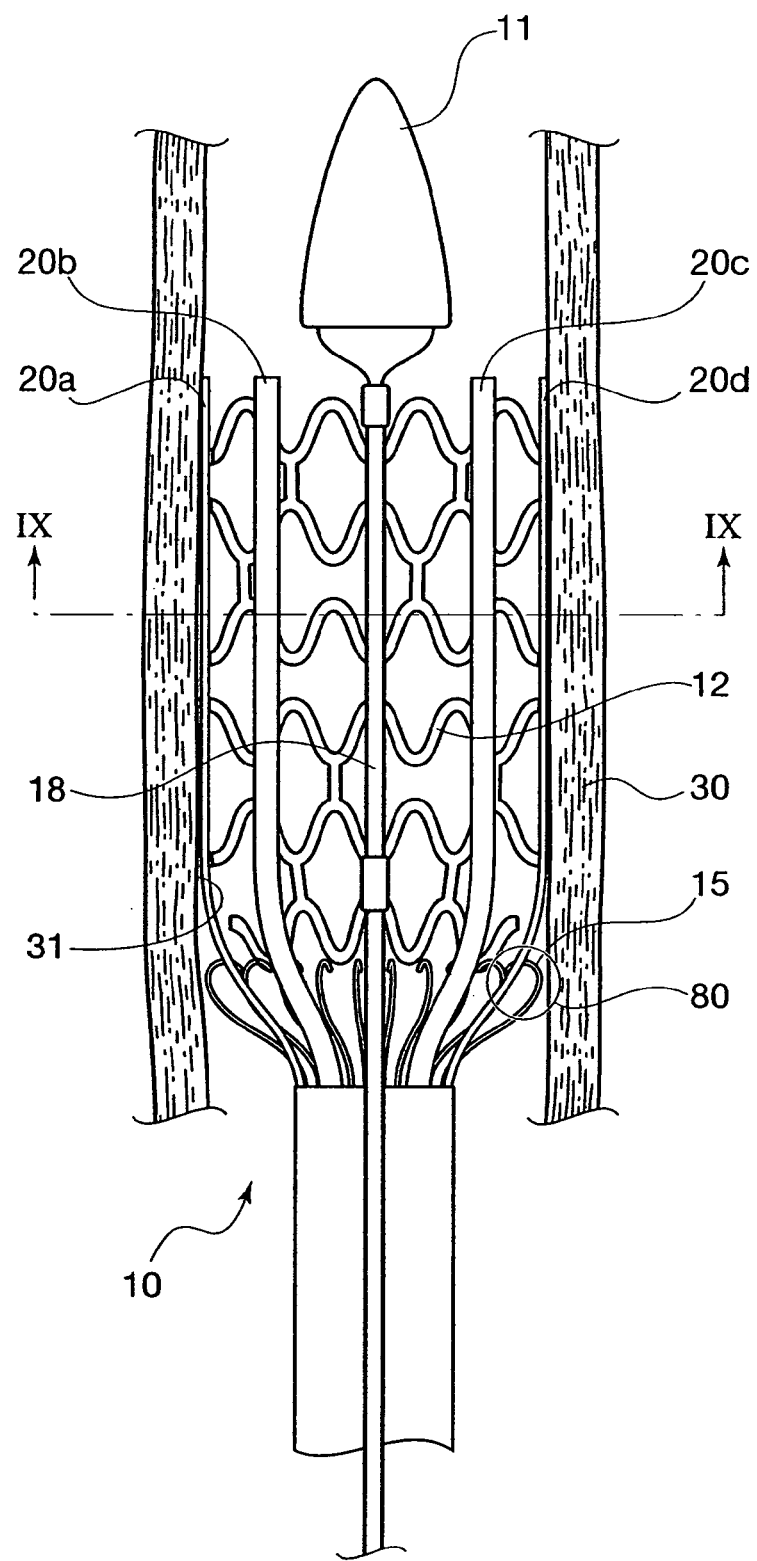
FIG. 8 shows a zoomed in view of a schematic cross-sectional representation of an exemplary embodiment of the present invention after a partial retraction of the outer sheath showing the SE stent and the inner sheath expanded before the retraction of the inner sheath.

FIG. 8 shows a zoomed-in view of a schematic cross-sectional representation of an exemplary embodiment of the present invention after a partial retraction of outer protective sheath 13 showing SE stent 12 and inner protective sheath 16 expanded before the retraction of inner protective sheath 16. Delivery system 10, including tip 11, outer protective sheath 13, inner protective sheath 16, and activator shaft 17, is shown in lumen wall 30 having lumen wall surface 31. Tails 20a, 20b, 20c, 20d, of inner protective sheath 16 are pressed by SE stent 12 against lumen wall surface 31 of lumen wall 30. Pusher springs 15 press against SE stent 12 to maintain SE stent 12 in position within lumen wall 30 during a possibly impending retraction of tails 20a, 20b, 20c, 20d. Zone 80 includes pusher spring 15 and represents a zoomed-in view shown in FIG. 10.

Figure 9:
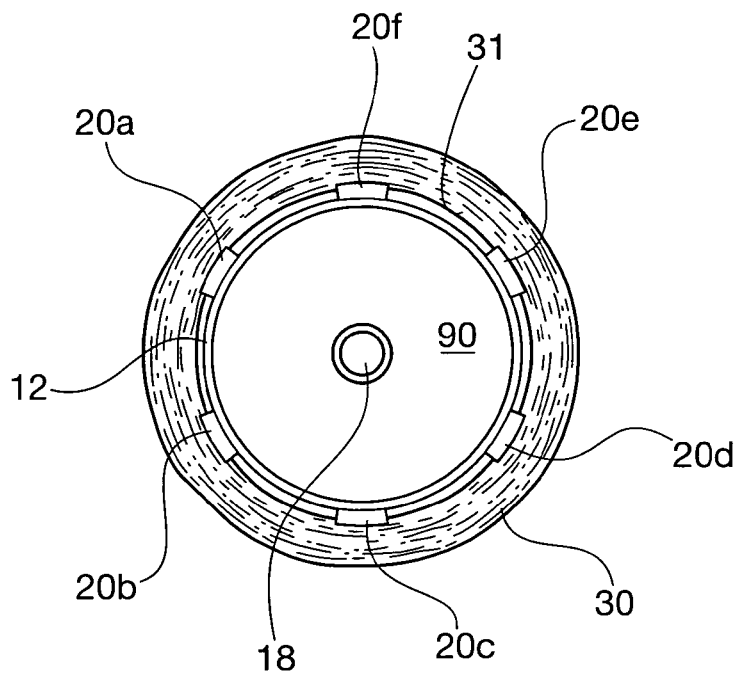
FIG. 9 shows the schematic cross-sectional representation of the exemplary embodiment of FIG. 8 cut along line IX-IX.

FIG. 9 shows the schematic cross-sectional representation of the exemplary embodiment of FIG. 8 cut along line IX-IX. In the center of FIG. 9 is central shaft 18 surrounded by lumen 90. Tails 20a, 20b, 20c, 20d, 20e, 20f of inner protective sheath 16 are pressed by SE stent 12 against lumen wall surface 31 of lumen wall 30. Tails 20a, 20b, 20c, 20d, 20e, 20f are equispaced around lumen wall surface 31, or may alternatively be in any other appropriate configuration.

Figure 10:
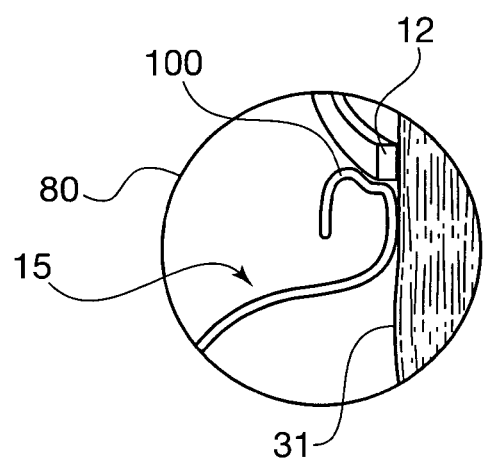
FIG. 10 shows a zoomed in view of the schematic cross-sectional representation of the exemplary embodiment of FIG. 8 showing a section of the expanded pusher spring.

FIG. 10 shows a zoomed-in view of the schematic cross-sectional representation of the exemplary embodiment of FIG. 8 showing zone 80 including pusher spring 15. Pusher spring 15 abuts SE stent 12 to maintain SE stent 12 in position against lumen wall surface 31. Pusher spring 15 is shown in FIG. 10 having depression 100 to prevent SE stent 12 from moving between pusher spring 15 and lumen wall surface 31 during a retraction of the tails of an inner protective sheath.

Figure 11:
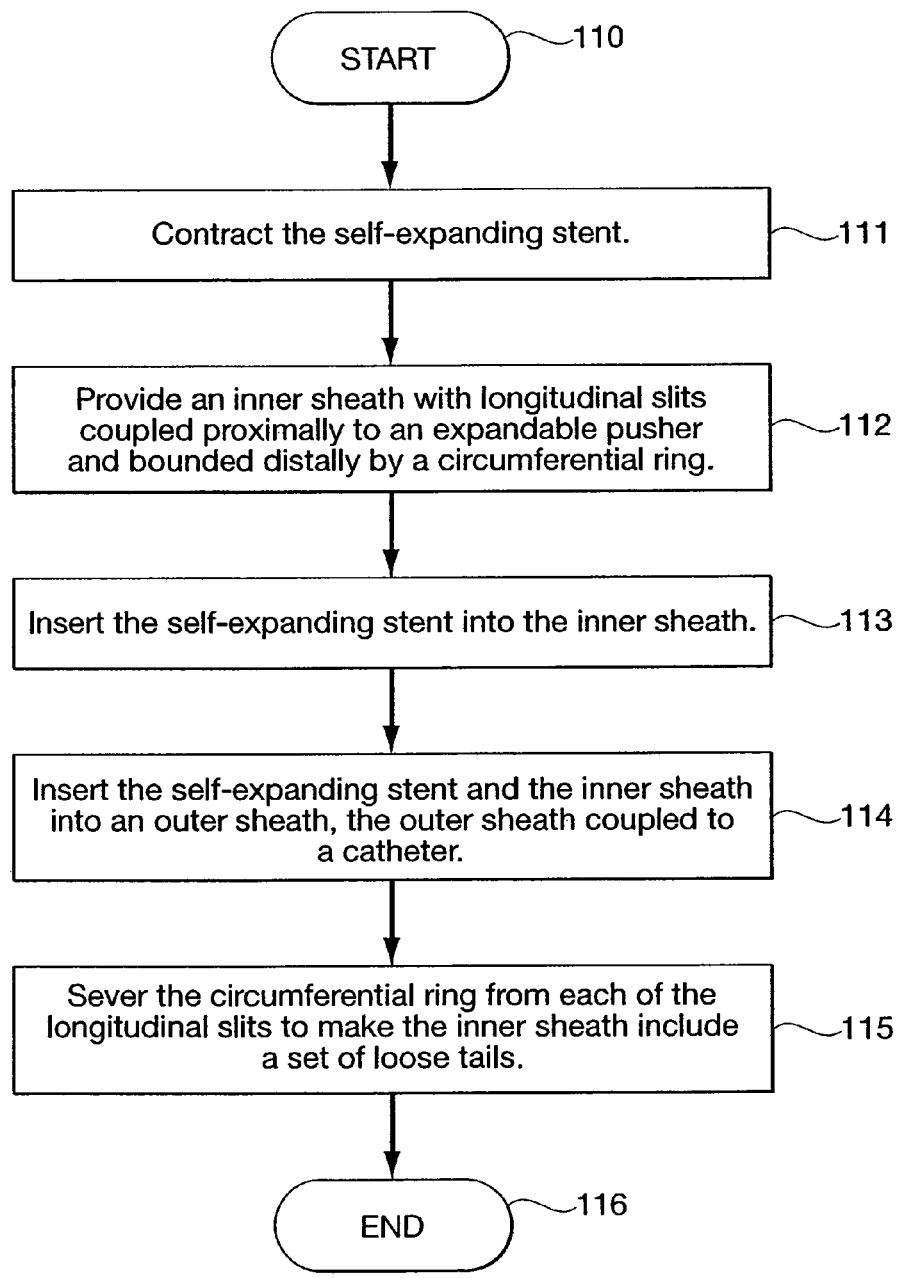
FIG. 11 is a flow chart illustrating an exemplary method for manufacturing an exemplary embodiment of the present invention.

FIG. 11 is a flow chart illustrating an exemplary method for manufacturing an exemplary embodiment of the present invention. The flow in FIG. 11 starts in start circle 110 and proceeds to action 111, which indicates to contract the self-expanding stent. From action 111 the flow proceeds to action 112, which indicates to provide an inner sheath with longitudinal slits coupled proximally to an expandable pusher and bounded distally by a circumferential ring. From action 112 the flow proceeds to action 113, which indicates to insert the self-expanding stent into the inner sheath. From action 113 the flow proceeds to action 114, which indicates to insert the self-expanding stent and the inner sheath into an outer sheath. The outer sheath may be coupled to a catheter. From action 114 the flow proceeds to action 115, which indicates to sever the circumferential ring from each of the longitudinal slits to make the inner sheath include a set of loose tails. From action 115 the flow proceeds to end circle 116.

Figure 12:
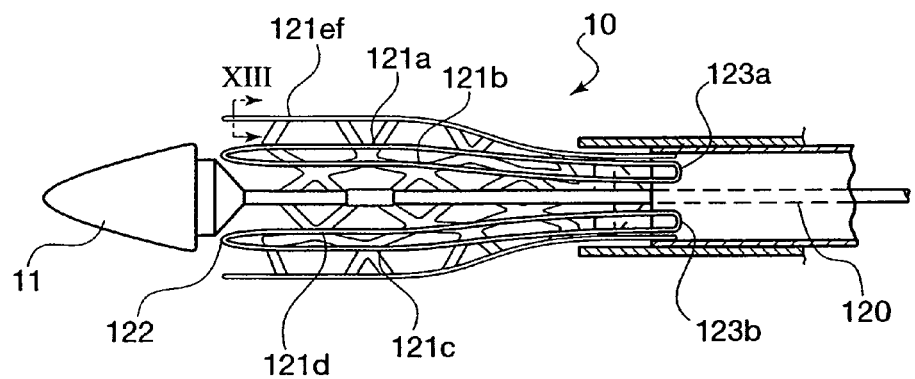
FIG. 12 shows a schematic cross-sectional representation of another exemplary embodiment of the present invention after a partial retraction of the outer sheath showing the SE stent partially expanded and looped wires attached to a proximal inner sheath.

FIG. 12 shows a schematic cross-sectional representation of another exemplary embodiment of the present invention after a partial retraction of the outer sheath showing the SE stent partially expanded. Delivery system 10 includes tip 11 and looped wires 121a, 121b, 121c, 121d, 121e, 121f attached to proximal inner sheath 120. More or fewer looped wires may also be provided. Looped wires 121c, 121d are attached at a distal end at loop 122. Loop 122 may be a tight loop. Proximal inner sheath 120 includes anchor points 123a, 123b, which may anchor looped wires 121a, 121b, 121c, 121d, 121e, 121f to proximal inner sheath 120. Anchor points 123a, 123b may include a laser weld, a heat bond, or any other appropriate method of attachment. Looped wires 121a, 121b, 121c, 121d, 121e, 121f may be stainless steel, nitinol, elgiloy type metals, or any other appropriate material. Looped wires 121a, 121b, 121c, 121d, 121e, 121f may be roll-flattened to increase the load-bearing area of the wires, to increase the radial flexibility of the loops, and/or to reduce the cross-sectional area of delivery system 10. Increasing the radial flexibility of the wires of the loops may facilitate the complete opening and/or expansion of the stent upon deployment.

In another exemplary embodiment, loop 122 may be absent and looped wires 121c, 121d may not be connected at a distal end. In this exemplary situation, looped wires 121c, 121 d, as well as the other wires may terminate at a point or another appropriate shape.

Figure 13:
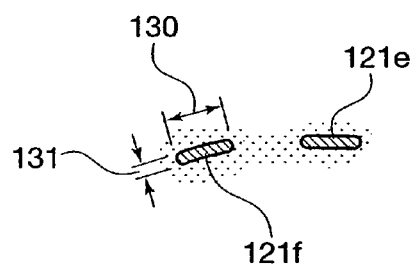
FIG. 13 shows the schematic cross-sectional representation of the exemplary embodiment of FIG. 12 cut along line XIII-XIII.

FIG. 13 shows the schematic cross-sectional representation of the exemplary embodiment of FIG. 12 cut along line XIII-XIII. Looped wires 121e, 121f are shown in cross-section and are roll-flattened. Width 130 of looped wire 121f may therefore be larger than depth 131 of looped wire 121f. In particular width 130 may be 0.004 inches and depth 131 may be 0.001 inches.

Figure 14:
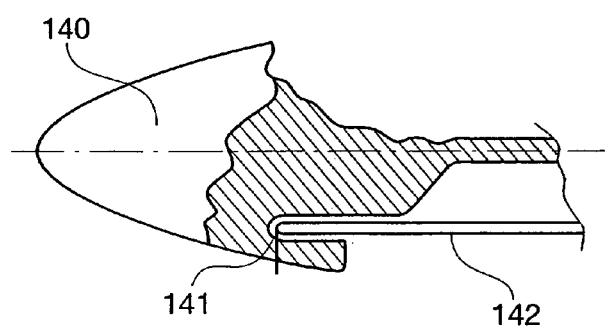
FIG. 14 shows a zoomed-in view of a schematic cross-sectional representation of another exemplary embodiment showing the molded tip of the medical appliance and the wires of an inner sheath.

FIG. 14 shows a zoomed-in view of a schematic cross-sectional representation of another exemplary embodiment showing molded tip 140 of the medical appliance and wire tail 142 of an inner sheath. Wire tail 142 is not looped and is situated in annular space 141 of molded tip 140. Positioning wire tail 142 in annular space 141 of molded tip 140 may enable the wires of an inner sheath to remain in proper position during deployment, and/or may protect wire tail 142 during deployment.

Alternative spaces may be provided in a molded tip for looped wires, and may therefore have a different shape and/or size.

As used herein, the term "therapeutic agent" includes one or more "therapeutic agents" or "drugs". The terms "therapeutic agents", "active substance" and "drugs" are used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences The therapeutic agent may be any pharmaceutically acceptable agent such as a non-genetic therapeutic agent, a biomolecule, a small molecule, or cells.

Exemplary non-genetic therapeutic agents include antithrombogenic agents such heparin, heparin derivatives, prostaglandin (including micellar prostaglandin E1), urokinase, and PPack (dextrophenylalanine proline arginine chloromethyl ketone); antiproliferative agents such as enoxaparin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; antineoplastic/antiproliferative/antimitotic agents such as paclitaxel, epothilone, cladribine, 5-fluorouracil, methotrexate, doxorubicin, daunorubicin, cyclosporine, cisplatin, vinblastine, vincristine, endostatin, trapidil, halofuginone, and angiostatin; anticancer agents such as antisense inhibitors of c-myc oncogene; antimicrobial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamicin, rifampin, minocycline, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anticoagulants such as D-Phe-Pro-Arg chloromethyl ketone, an RGD peptide-containing compound, heparin, antithrombin compounds, platelet receptor antagonists, antithrombin antibodies, antiplatelet receptor antibodies, enoxaparin, hirudin, warfarin sodium, dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA encoding them. Non-limiting examples of genes include survival genes that protect against cell death, such as anti-apoptotic Bcl-2 family factors and Akt kinase; serca2 gene; and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin-like growth factor. A non-limiting example of a cell cycle inhibitor is a cathepsin D (CD) inhibitor. Non-limiting examples of antirestenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds that have a molecular weight of less than 100 kD.

Exemplary cells include stem cells, progenitor cells, endothelial cells, adult cardiomyocytes, and smooth muscle cells. Cells can be of human origin (autologous or allogeneic) or from an animal source (xenogeneic), or genetically engineered. Non-limiting examples of cells include side population (SP) cells, lineage negative (Lin−) cells including Lin−CD34−, Lin−CD34+, Lin−c Kit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, GØ cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone, including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and copolymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A self-expanding stent in combination with a delivery system for delivering and deploying the self-expanding stent comprising:
    a self-expanding stent, the stent having a distal end;
    an outer sheath adapted to hold the self-expanding stent in an interior space before deployment of the self-expanding stent, said outer sheath having a delivery position in which it constrains the self-expanding stent and a retracted position in which it is retracted from and releases the self-expanding stent;
    an inner sheath located within the outer sheath and adapted to be arranged about the self-expanding stent before deployment of the self-expanding stent, said inner sheath comprising a set of expandable elements, said inner sheath having an unexpanded position in which it is located within the outer sheath and an expanded position after the outer sheath has been retracted to its retracted position;
    wherein the expandable elements extend distally to the distal end of the self-expanding stent or distally beyond the distal end of the self-expanding stent when the inner sheath is in the unexpanded position and when the inner sheath is in the expanded position;
    an expandable pusher configured to abut a proximal end of the self-expanding stent, said expandable pusher having a contracted position in which it is held within the outer sheath when the outer sheath is in the delivery position and an expanded position to which it expands after the outer sheath has been retracted to its retracted position, wherein the expandable pusher comprises a set of pusher springs, wherein a distal end of the set of pusher springs abuts the proximal end of the self-expanding stent and extend proximally therefrom;
    wherein a portion of the set of pusher springs extends radially inward;
    a two-stage retraction mechanism coupled to the outer sheath and the inner sheath that proximally retracts the outer sheath and the inner sheath, the two-stage retraction mechanism being configured to retract the outer sheath fully before retracting the inner sheath; and
    wherein the set of pusher springs of the expandable pusher that abuts the proximal end of the self-expanding stent is configured to maintain the longitudinal position of the self-expanding stent during retraction of the inner sheath.

2. The stent and delivery system of claim 1, wherein the expandable elements of the inner sheath are biodegradable, and wherein after deployment of the self-expanding stent the expandable elements of the inner sheath have a decoupled position in which they are not in contact with any portion of the delivery system other than the stent.

3. The stent and delivery system of claim 1, wherein the set of expandable elements of the inner sheath comprises a plurality of inner sleeve tails.

4. The stent and delivery system of claim 1, wherein the set of expandable elements of the inner sheath comprises a plurality of wires.

5. The stent and delivery system of claim 4, further comprising:
   a molded tip arranged distal to the outer sheath and the self-expanding stent before deployment, wherein the molded tip includes an annular space for housing an end of each of the plurality of wires.

6. The stent and delivery system of claim 4, wherein each of the wires is attached at a distal end to another of the wires to form a wire loop.

7. The stent and delivery system of claim 4, wherein the wires are roll-flattened to reduce a radial displacement of the wires.

8. The stent and delivery system of claim 1, wherein the self-expanding stent comprises a coating including a bioactive agent.

9. The stent and delivery system of claim 1, wherein the inner sheath further has a retracted position in which it is retracted from the self-expanding stent after the inner sheath has expanded to its expanded position.

10. The stent and delivery system of claim 9, wherein, when said inner sheath is retracted from its expanded position to its retracted position, the expandable pusher is in its expanded position and abuts the end of the self-expanding stent.

11. The stent and delivery system of claim 1, wherein at least some of the pusher springs include depressions configured to prevent the self-expanding stent from moving between the at least some of the pusher springs and the lumen wall during retraction of the inner sheath.

12. A self-expanding stent in combination with a delivery system for delivering and deploying the self-expanding stent comprising:
   a self-expanding stent, having a distal end;
   an outer sheath adapted to hold the self-expanding stent in an interior space before deployment of the self-expanding stent, said outer sheath having a delivery position in which it constrains the self-expanding stent and a retracted position in which it is retracted from and releases the self-expanding stent;
   an inner sheath located within the outer sheath and adapted to be arranged about the self-expanding stent before deployment of the self-expanding stent, said inner sheath comprising a set of expandable elements, said inner sheath having an unexpanded position in which it is located within the outer sheath and an expanded position after the outer sheath has been retracted to its retracted position;
   wherein the expandable elements extend distally to the distal end of the self-expanding stent or distally beyond the distal end of the self-expanding stent when the inner sheath is in the unexpanded position and when the inner sheath is in the expanded position;
   wherein after deployment of the self-expanding stent the expandable elements of the inner sheath have a decoupled position in which they are not in contact with any portion of the delivery system other than the stent; and
   an expandable pusher having a distal end that abuts a proximal end of the self-expanding stent and that extends proximally from the self-expanding stent, said expandable pusher having a contracted position in which it is held within the outer sheath when the outer sheath is in the delivery position and an expanded position to which it expands after the outer sheath has been refracted to its retracted position, wherein the expandable pusher includes a set of pusher springs, wherein a distal end of the set of pusher springs abuts the proximal end of the self-expanding stent and wherein a portion of the set of pusher springs extends radially inward and wherein the set of pusher springs that abut the proximal end of the self-expanding stent is configured to maintain the self-expanding stent in position during deployment of the self-expanding stent.

13. The stent and delivery system of claim 12, wherein the expandable elements of the inner sheath are biodegradable.

14. The stent and delivery system of claim 12, wherein the set of expandable elements of the inner sheath comprises a plurality of inner sleeve tails.

15. The stent and delivery system of claim 12, wherein the set of expandable elements of the inner sheath comprises a plurality of wires.

16. The stent and delivery system of claim 15, further comprising:
   a molded tip arranged distal to the outer sheath and the self-expanding stent before deployment, wherein the molded tip includes an annular space for housing an end of each of the plurality of wires.

17. The stent and delivery system of claim 15, wherein each of the wires is attached at a distal end to another of the wires to form a wire loop.

18. The stent and delivery system of claim 15, wherein the wires are roll-flattened to reduce a radial displacement of the wires.

19. The stent and delivery system of claim 12, wherein the self-expanding stent comprises a coating including a bioactive agent.

* * * * *

UNITED STATES PATENT AND TRADEMARK OFFICE
CERTIFICATE OF CORRECTION

| | |
|---|---|
| PATENT NO. | : 7,918,880 B2 |
| APPLICATION NO. | : 11/059240 |
| DATED | : April 5, 2011 |
| INVENTOR(S) | : Michael Austin |

It is certified that error appears in the above-identified patent and that said Letters Patent is hereby corrected as shown below:

IN THE CLAIMS:

Column 16, Claim 12
Line 17, delete "refracted", and insert therefor -- retracted --.

Signed and Sealed this
Seventeenth Day of May, 2011

David J. Kappos
*Director of the United States Patent and Trademark Office*